United States Patent [19]

Plona

[11] 4,283,953
[45] Aug. 18, 1981

[54] METHOD AND APPARATUS FOR DETERMINING A GRANULARITY PROPERTY OF A SUBSURFACE FORMATION AROUND A BOREHOLE

[75] Inventor: Thomas J. Plona, Brookfield, Conn.

[73] Assignee: Schlumberger Technology Corporation, New York, N.Y.

[21] Appl. No.: 83,104

[22] Filed: Oct. 18, 1979

Related U.S. Application Data

[63] Continuation-in-part of Ser. No. 955,821, Oct. 30, 1978, abandoned.

[51] Int. Cl.$^3$ ............................................. G01N 29/00
[52] U.S. Cl. ...................................... 73/589; 73/599; 367/86
[58] Field of Search .................. 73/574, 579, 589, 599, 73/600, 618, 620, 627, 629; 367/25, 26, 32, 35, 86

[56] References Cited

U.S. PATENT DOCUMENTS

| 2,848,891 | 8/1958 | Hunter, Jr. et al. | 73/600 |
| 3,211,252 | 10/1965 | Smith, Jr. et al. | 73/610 |
| 3,588,800 | 6/1971 | Moore et al. | 367/86 |
| 3,747,702 | 7/1973 | Beil | 367/87 |
| 3,883,841 | 5/1975 | Moore et al. | 73/589 |
| 3,996,791 | 12/1976 | Niklas et al. | 73/602 |
| 4,026,157 | 5/1977 | Goebbels | 73/599 |
| 4,168,483 | 9/1979 | Parthasarathy et al. | 367/26 |

OTHER PUBLICATIONS

Papadakis, "Revised Grain–Scattering Formulas and Tables", *Journal of Acoustical Society of America*, vol. 37, No. 4, pp. 703–710, Apr. 1965.
Papadakis, "Ultrasonic Attenuation Caused by Scattering in Polycrystalline Metals", Journal of Acoustical Society of America, vol. 37, No. 4, pp. 711–717, Apr. 1965.
K. Goebbels et al., Quantitative Determination of Grain Size and Detection of Inhomogeneities in Steel by Ultrasonic Backscattering Measurements, pp. 1–19.
B. Fay, "Ultrasonic Back-Scattering, Method for Non-Destructive Structure Testing", Ultrasonics Symposium Proceedings, (1976), IEEE, Cat. 76CH1120-5SU, pp. 51–53.
G. Johnson et al., "Numerical Computations of Elastic Scattering Cross Sections", Journal of Applied Physics, vol. 36, No. 11, pp. 3466–3475, Nov. 1965.

*Primary Examiner*—Stephen A. Kreitman
*Attorney, Agent, or Firm*—William R. Sherman; Stephen L. Borst; Louis H. Reens

[57] ABSTRACT

Techniques for a broad band high frequency acoustic investigation of a subsurface formation around a borehole are described utilizing a range of acoustic frequencies selected to produce detectable acoustic backscatter from grains within the subsurface formation. The acoustic backscatter is detected and a spectrum thereof is produced and averaged over adjacent subsurface formation regions. A subsurface formation parameter such as the frequency dependency of the attenuation of the backscatter is determined from an analysis of the spectrum to provide an indication of the granularity property of the subsurface formation. Use of a broad range of frequencies enables a determination of the subsurface formation parameter over a large range of grain sizes. In another technique the spectrum of the detected backscatter is modified to remove the effect of the frequency response of the system with which the investigation is made. The modified spectrum may then be used to derive an indication of the granularity property of the subsurface earth formation such as its mean grain size or grain size distribution.

28 Claims, 10 Drawing Figures

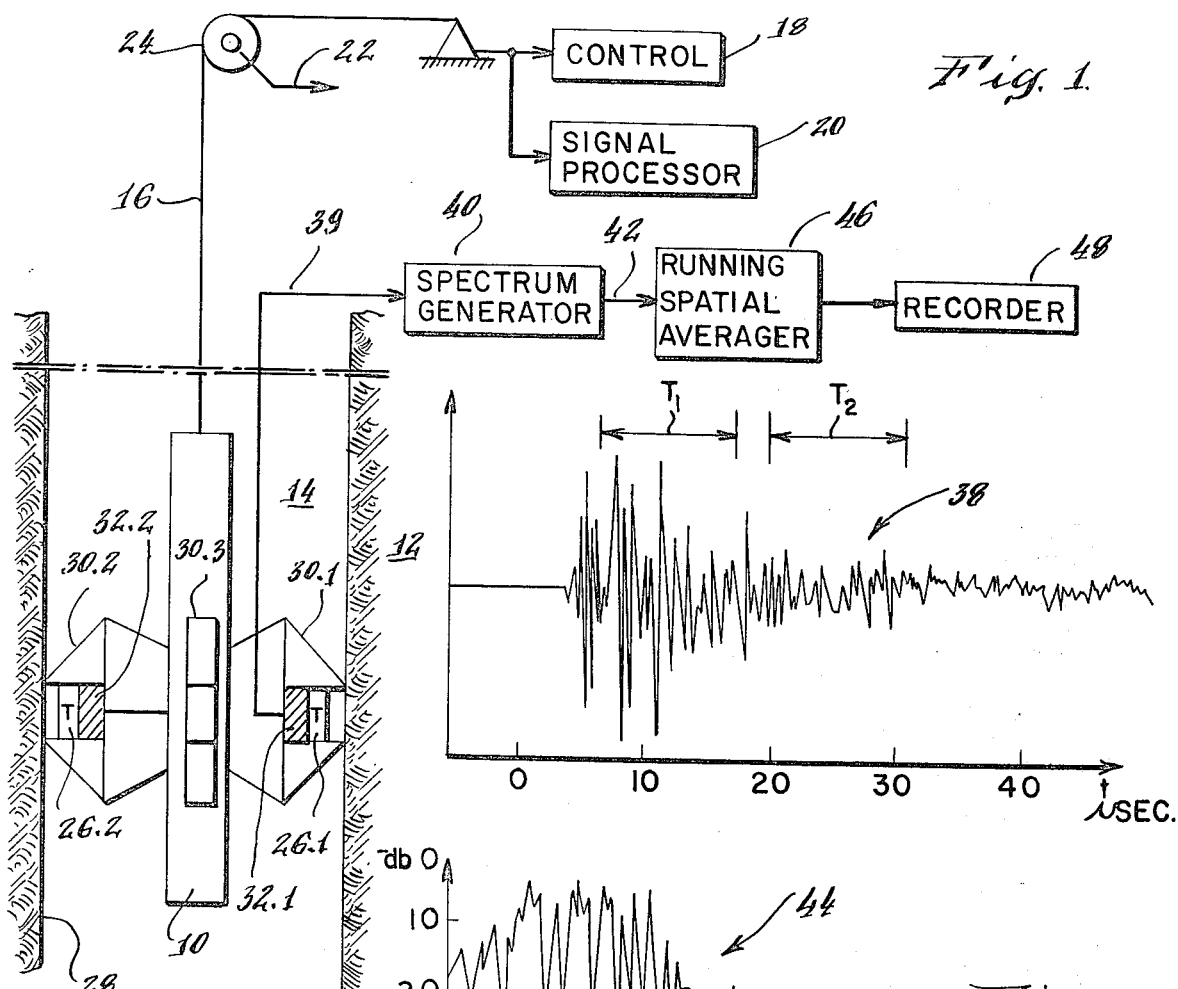
Fig. 1.
Fig. 1A.
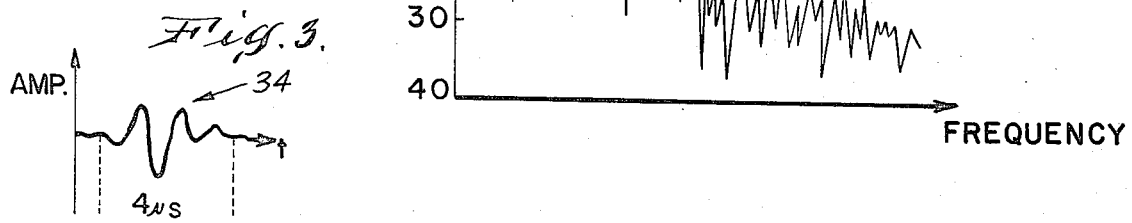
Fig. 3.
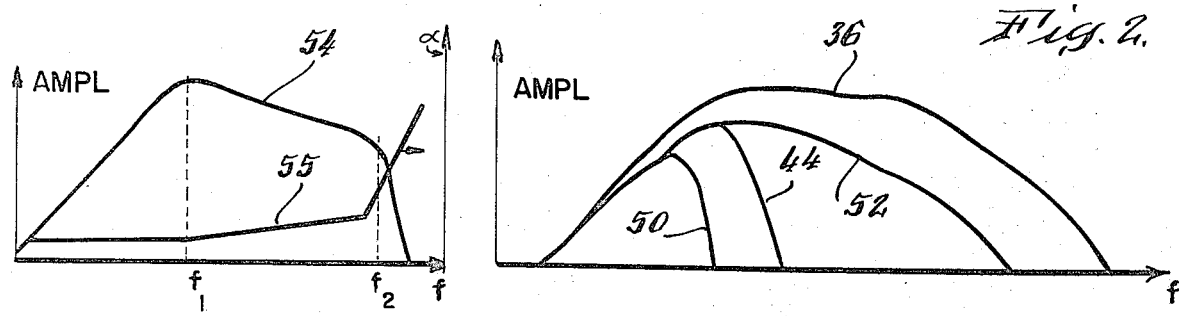
Fig. 4.
Fig. 2.

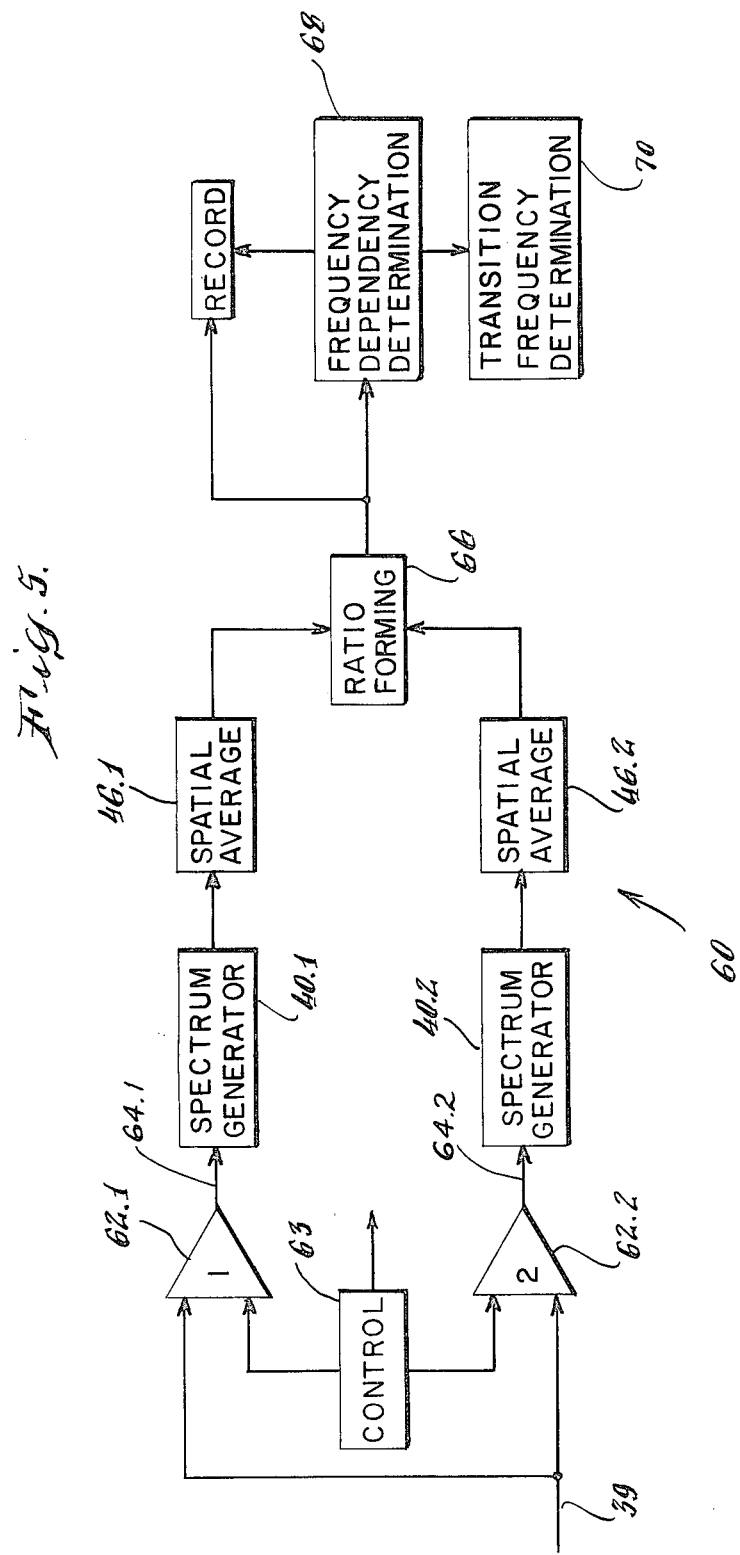

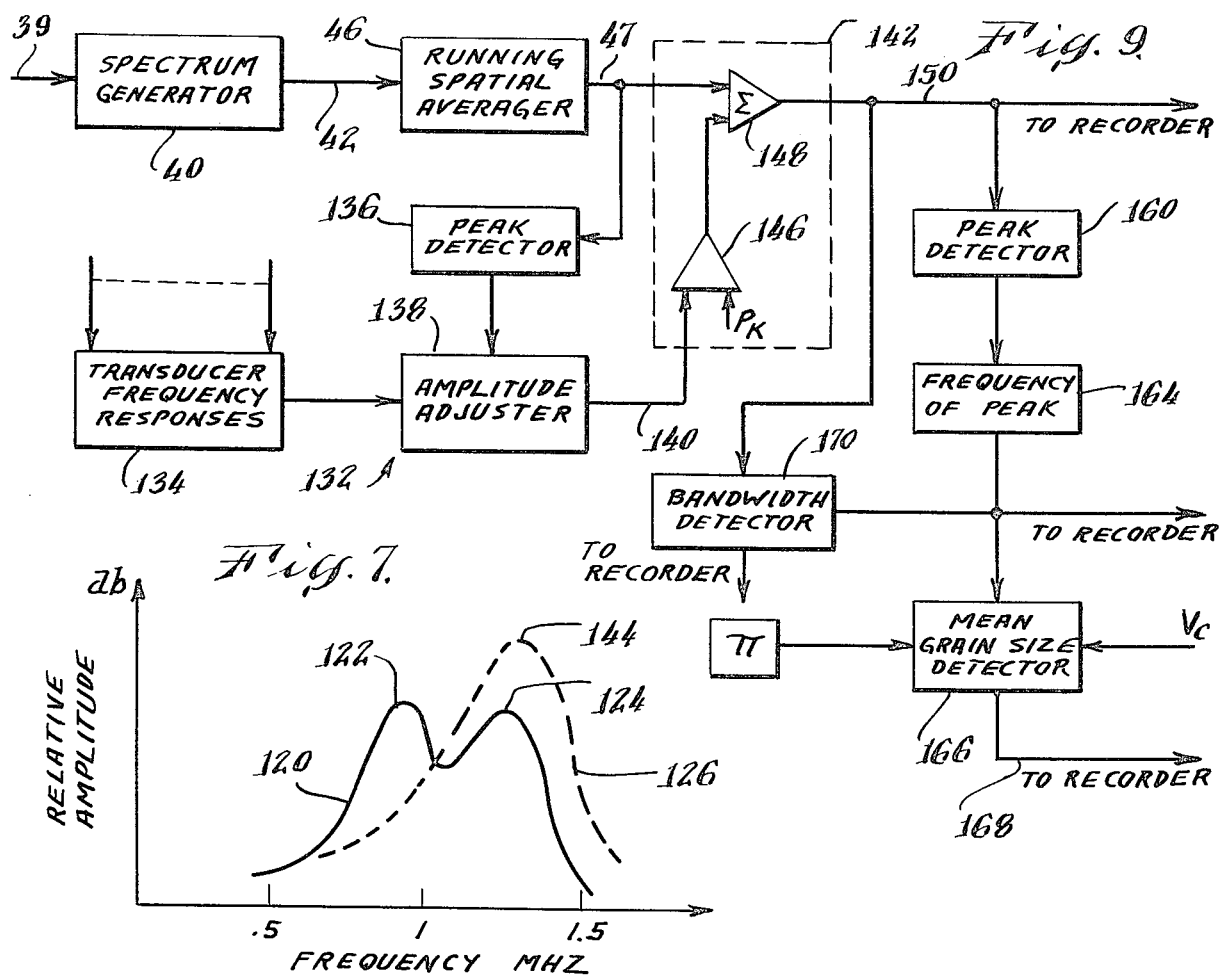
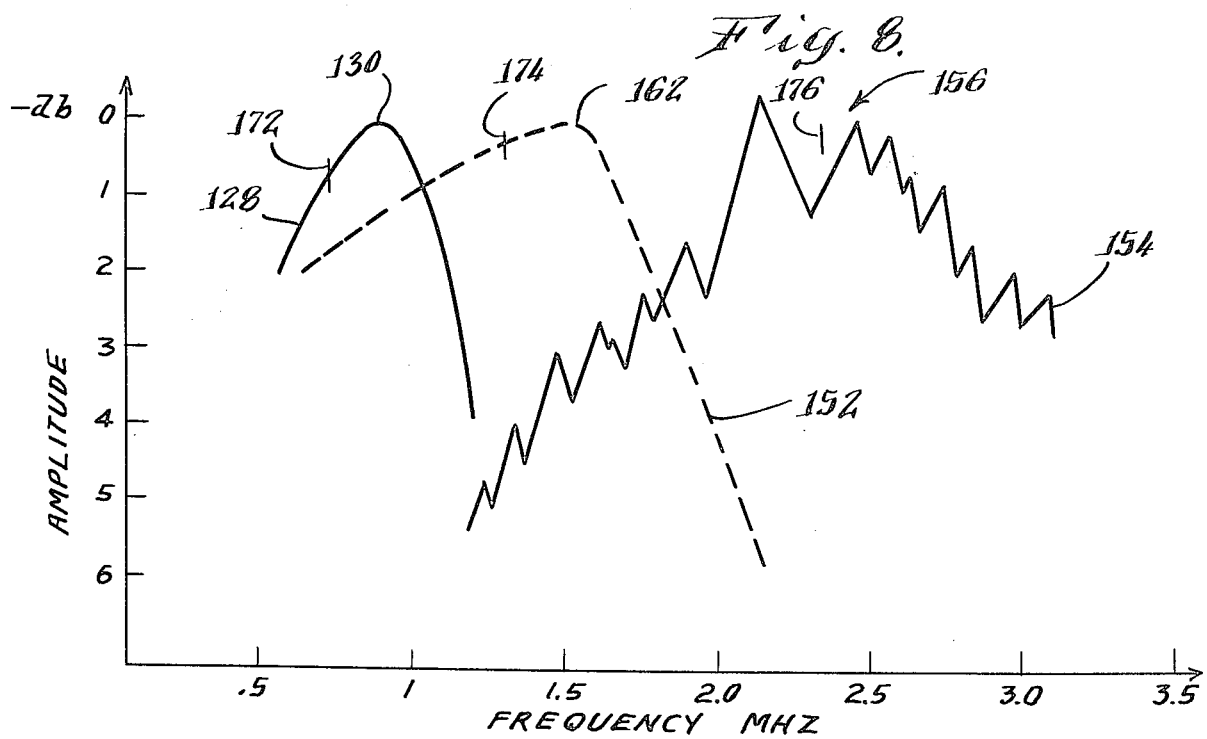

METHOD AND APPARATUS FOR DETERMINING A GRANULARITY PROPERTY OF A SUBSURFACE FORMATION AROUND A BOREHOLE

This application is a continuation in part of U.S. patent application Ser. No. 955,821, filed Oct. 30, 1978, now abandoned.

FIELD OF THE INVENTION

This invention relates to the investigation of a borehole in an earth formation utilizing ultrasonic techniques at backscatter frequencies. More specifically, this invention relates to a method and apparatus for deriving an indication of a granularity property of porous subsurface earth formations around a borehole.

BACKGROUND OF THE INVENTION

In the exploration of porous subsurface earth formations around boreholes, it is of significant value to be able to obtain information about the granularity property of the subsurface formation. For example, information which may lead to determination of the presence of small grains, grain size distribution, or grain orientations or changes of these formation parameters from one zone to another can be quite useful in evaluating an earth formation for its ability to yield hydrocarbons.

Proposals have been made to measure mean grain sizes in usually finely grained materials utilizing ultrasonic techniques at scatter frequencies. For example, in articles entitled "Revised Grain-Scattering Formulas and Tables" and "Ultrasonic Attenuation Caused by Scattering in Polycrystalline Metals" by E. P. Papadakis and published in *The Journal of the Acoustical Society of America*, Volume 37, Number 4, pages 703-717 during April 1965, the frequency and grain size dependence of ultrasonic attenuation are described for a variety of materials.

Thus it is recognized that a frictional attenuation, $\alpha_a$, of sound is directly proportional to frequency up to those frequencies where scattering effects occur. At scatter frequencies the attenuation becomes a function of mean grain diameter as well. Thus, at scatter frequencies attenuation includes both absorptive $\alpha_a$ and scatter effects, $\alpha_s$. The latter, $\alpha_s$, is dependent upon frequency and grain size in a manner generally described as:

(1) For $\lambda >> \bar{d}$, $\alpha_s$ varies according to $\bar{d}^3 f^4$
(2) For $\lambda \approx \bar{d}$, $\alpha_s$ varies according to $\bar{d} f^2$
(3) For $\lambda < \bar{d}$, $\alpha_s$ varies according to $1/\bar{d}$ where $\lambda$ is the wavelength of the ultrasonic energy in the material, $\bar{d}$ the mean grain diameter and $f$ the frequency of the ultrasonic energy.

Such known and predictable effect of homogeneous nonporous substances on ultrasonic energy has led to a specific ultrasonic energy backscatter technique for quantitativly measuring the grain size of a homogeneous specimen as described in the U.S. Pat. No. 4,026,157 to Goebbels. In accordance with this patent, sequential bursts of acoustic energy at respectively two different specific scatter frequencies are directed at a specimen for which the frequency dependency of the scatter attenuation is predictable. The transducer is oriented in a particular manner to enhance the generation of shear waves in the specimen, which may be so thin as to cause reflections from both upper and lower surfaces. Relative motion between the specimen and the transducer is maintained to average out interference maxima and minima. The acoustic backscatter energy is detected and used to derive amplitude attenuation plot for an apparently known acoustic path length. The measured attenuation at the two frequencies is then used to obtain a measurement of the grain size based upon the known frequency dependency of the attenuation at the two different frequencies.

A porous subsurface formation around a borehole does not exhibit a predictable frequency dependency like a carefully prepared specimen as described in the Goebbels patent. A specimen as described by the latter tends to be of a homogeneous character with closely spaced grains without voids or pores. In the exploration of a subsurface formation, however, one is interested in those rock formations where there exists a porosity capable of retaining hydrocarbons. Such porous subsurface formation is likely to be granular. The presence of porosity, however, affects the backscatter of ultrasonic energy, particularly at those frequencies which are highly sensitive to grain size. Furthermore, a subsurface formation is likely to have grains whose sizes may vary a great deal. Though for any narrow zone such grains may appear relatively consistent in size, the change in size from zone to zone as well as changes in orientation influence the amplitude and frequency of the backscatter signals. Hence, a direct measurement of the grain size as proposed in the Goebbels patent with different pulses at separate and discrete frequencies is not normally feasible for a porous subsurface formation.

A substantial body of prior art patents and literature exists related to ultrasonic nondestructive testing techniques. Such testing may include pulse echo techniques with spectrascopic investigations such as described, for example, in "Research Techniques in Nondestructive Testing" by R. S. Sharpe, published by Academic Press in 1970. With particular references to pages 43 through 53 therein, various spectra for different grain sizes of a material are illustrated. It is recognized that an accurate knowledge of the frequency response of the ultrasonic transducer is needed to evaluate the spectrum of echoes. The spectra are described as indicative of high attenuation characteristics of certain materials over particular frequencies. In theoretical treatises it has been shown that a single spherical object backscatters acoustic energy with maximum effect at a wavelength which approximates the diameter of the object. See, for example, articles "Numerical Computations of Elastic Scattering Cross-Sections" by G. Johnston and R. Truell, published in the *Journal of Applied Physics*, Volume 36, No. 11, pages 3466-3473, November, 1965 and "Analysis of Echoes from a Solid Elastic Sphere in Water" by R. Hickling and published in *The Journal of the Acoustical Society of America*, Vol. 34, No. 10, pages 1582-1592, October 1962; and "Ultrasonic Back-Scattering, A Method For Non-Destructive Structure Testing" by B. Fay, published at pages 51-53 in the 1976 Ultrasonics Symposium Proceedings of the IEEE, (Cat. No. 76 CH1120-5SU).

In prior art acoustic investigations of carefully prepared specimen at backscatter frequencies, the noise, i.e. the large peaks and valleys, both in the amplitude and the frequency domain, render meaningful analysis particularly difficult. When subsurface formations are investigated at backscatter frequencies, additional factors such as large grain size variations and porosity are introduced which strongly affect the acoustic backscatter.

SUMMARY OF THE INVENTION

In a technique in accordance with the invention for investigating a porous subsurface formation around a borehole, an indication of a subsurface parameter such as a granularity property of the formation is obtained by directing acoustic pulses containing a broad spectrum of ultrasonic scatter frequencies at the formation and detecting acoustic backscatter energy caused by the pulses. The frequency bandwidth of the ultrasonic pulses is so selected that detectable acoustic backscatter energy occurs with, in accordance with one embodiment, an attenuation whose frequency dependency characterizes the formation parameter.

As described herein with reference to one technique in accordance with the invention for characterizing the granularity of the subsurface formation, a spectra of signals representative of the acoustic backscatter energy are generated. The amplitudes of frequency components in the spectra are then analyzed to obtain an indication of the frequency dependency of the attenuation of the acoustic backscatter energy.

For example, if the frequency dependency of the attenuation indicates a fourth power behavior, then a coarse conclusion can be made that the subsurface formation is in fact granular. A more precise evaluation may reveal a shift in the frequency range where this fourth power behavior occurs in comparison with the frequency dependency of the attenuation in nearby zones; thus indicating a possible change in grain size, with an upward shift in frequency being indicative of smaller grain size and a lower shift likely to indicate a larger grain size. In this manner an indication of depositional cycles of subsurface formation zone can be obtained.

In one technique in accordance with the invention for determining the frequency dependency of the attenuation of the subsurface formation, the acoustic backscatter energy is analyzed during separate intervals. Spectra of the intervals are generated and each spectrum is separately averaged over a spatial region of the borehole. Ratios between corresponding frequency components in the averaged spectra of the intervals are generated to indicate attenuation per unit distance as a function of frequency. The frequency dependence of the attenuation may then be determined with a slope detector or curve fitting technique to characterize a granularity of the subsurface formation.

In an apparatus in accordance with the invention for determining a subsurface formation parameter such as a granularity property of formation, signals representative of acoustic backscatter energy caused by acoustic pulses covering a range of frequencies as previously described, are passed through a bank of passband filters. The filters are tuned to sequential bands across the range of frequencies employed in the broad band ultrasonic investigation. The outputs of the filters are then integrated and sampled to obtain an indication of the frequency dependency of the attenuation and thus a granularity property of the subsurface formation.

In another technique in accordance with the invention the frequency spectrum of acoustic backscatter is used to yield a frequency or range of frequencies that relate in a particular manner to a granular property of the subsurface formation. For example, as described herein for one such technique, an acoustic pulse is employed to introduce acoustic energy at backscatter wavelengths estimated to generally correspond with a mean dimension of the grains such as their diameter. The resulting acoustic backscatter is detected and a signal representative thereof produced. The frequency spectrum of the backscatter signal is modified to remove the effect of the frequency response of the system used to make the acoustic investigation. A peak in the modified spectrum characterizes the presence of a dominant grain size in the subsurface formation and the broadness of the peak, its bandwidth, provides an indication of the distribution of grain sizes. By conducting such acoustic backscatter investigation over a broad range of frequencies, an indication of grain sizes can be obtained for various sizes.

It is, therefore, an object of the invention to provide a method and apparatus for determining a subsurface formation parameter which characterizes a granularity property of the subsurface formation around a borehole.

These and other advantages and objects of the invention can be understood from the following description of several embodiments described in conjunction with the drawings.

BRIEF DESCRIPTION OF DRAWINGS

FIG. 1 is a schematic block diagram of an apparatus in accordance with the invention with an illustrative time-amplitude plot of a backscatter signal;

FIG. 1A is an amplitude frequency plot of the spectrum of an unaveraged backscatter signal obtained in accordance with the invention;

FIG. 2 is an amplitude-frequency plot of various illustrative signals generated in the apparatus of FIG. 1;

FIG. 3 is an illustrative waveform of an ultrasonic pulse used to investigate the subsurface formation around a borehole with a broad range of frequencies selected to cause acoustic backscatter from which an indication of the granularity of the formation can be derived;

FIG. 4 is an illustrative amplitude-frequency plot of an acoustic backscatter signal exhibiting several frequency dependencies, and a plot of attenuation as a function of frequency;

FIG. 5 is a schematic block diagram of a technique in accordance with the invention for determining the frequency dependency of attenuation in an acoustic backscatter signal to derive a granularity property of a subsurface formation;

FIG. 7 is a relative amplitude-frequency plot of an acoustic backscatter signal and the frequency response of a transducer and amplifier system employed;

FIG. 8 is a relative amplitude-frequency plot of several modified backscatter signals obtained from an acoustic investigation of different subsurface formations; and FIG. 9 is a schematic block diagram of another technique in accordance with the invention for determining a granularity property of the subsurface formation.

DETAILED DESCRIPTION OF EMBODIMENTS

Figure 6:
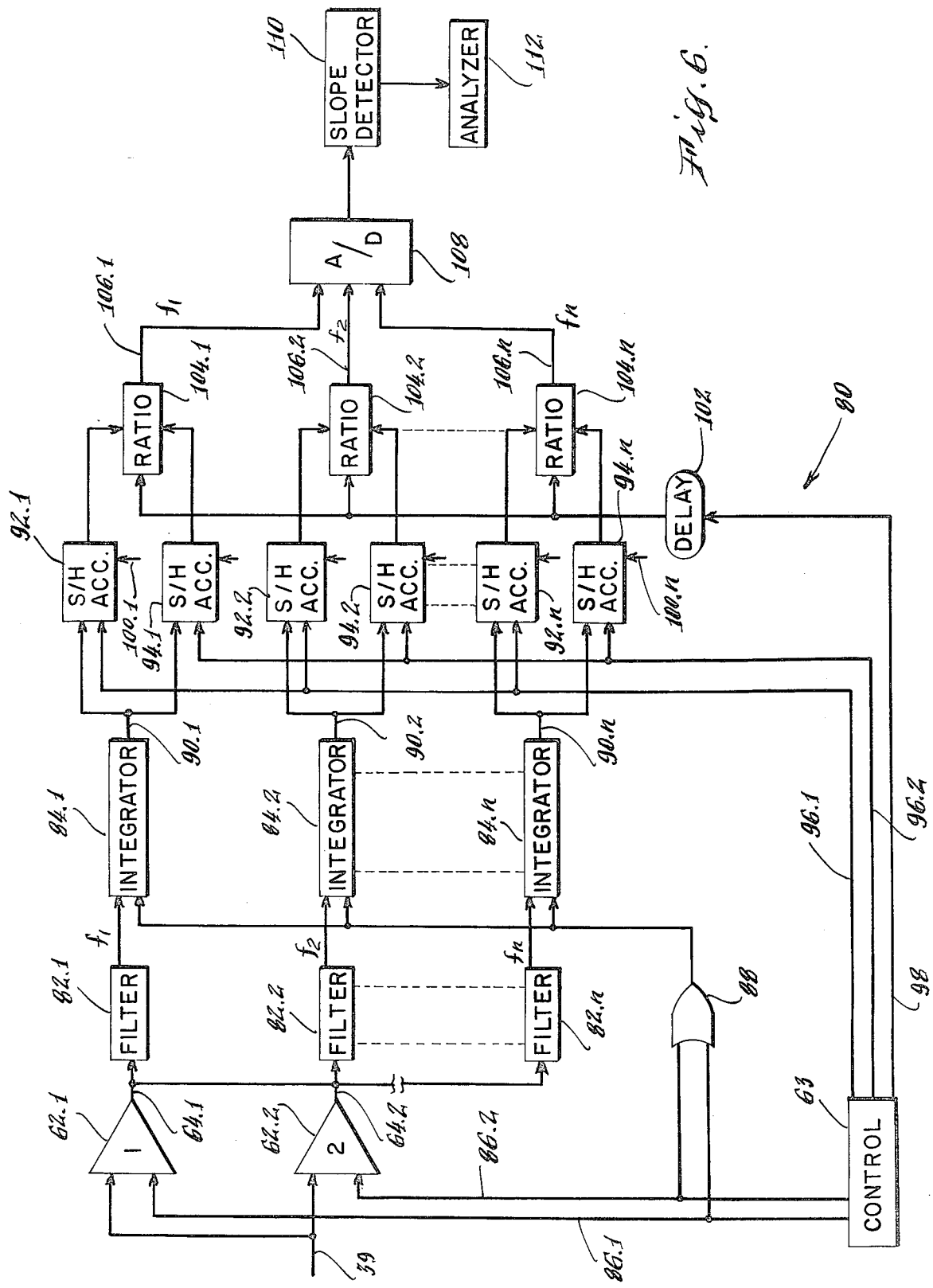
FIG. 6 is a schematic block diagram of an apparatus in accordance with the invention for determining a graularity property of a subsurface formation.

With reference to FIG. 1, a tool 10 for investigating the formation 12 around a borehole 14 is shown suspended from a cable 16. Surface located equipment such as 18 is provided to supply electrical power and control with a signal processor 20 which includes a display and a recorder. A depth signal is produced on a line 22 with a conventional apparatus 24 to indicate the location of tool 10 in borehole 14.

Tool 10 is provided with ultrasonic transducers 26 oriented to direct pulses of high frequency ultrasonic energy at the formation 12. The transducers 26 are spaced from the wall 28 of the formation so that there will be sufficient time separation between the trailing portion of the initial acoustic pulse and the subsequent backscatter signal from the subsurface formation. Transducers 26 may be mounted away from wall 28, but are shown mounted on wall engaging pads 30. There are a sufficient number of pads 30 to enable an investigation of the subsurface formation in different directions. In the embodiment of FIG. 1, four pads 30, equally angularly spaced around the borehole, are employed and each pad 30 has a transducer 26 and associated amplifiers with suitable control circuits 32.

Transducers 26 are of a broad bandwidth type capable of generating an acoustic pulse such as 34 whose waveform is shown in FIG. 3. The pulse 34 preferably generates a range of acoustic frequencies over a bandwidth covering the entire frequency spectrum of interest, namely those frequencies at which backscatter from subsurface formation grains occurs. This results in the need for a very broad bandwidth pulse, which may not be available from a single transducer if the range in grain sizes is also large. In such case additional transducers 26 can be employed to cover different frequency ranges.

For example, the spectrum of interest is primarily determined by sizes of the grains to be expected to be sensed in subsurface formation 12. The shape of the spectrum may thus depend upon grain sizes and acoustic velocity. If acoustic backscatter with frequency dependencies such as described in the art for absorbtive attenuation and fourth power attenuation are to be observed for subsurface formation grains of the order from about 0.05 mm to about 3.0 mm, the ultrasonic frequency spectrum generated by pulse 34 preferably should extend from about 100 KHz to about 30.0 MHz. This can be achieved with a number of transducers 26 each operating over a different range of frequencies.

Each transducer 26 preferably operates both as a broad band source of ultrasonic frequencies and a receiver for producing a signal representative of incident acoustic backscatter energy. A separate ultrasonic receiver could be employed, though the use of a common receiver and pulse generator is preferred. Since attenuation as a function of frequency is to be determined for the acoustic backscatter, the frequency response of a transducer 26 and amplifier 32 are predetermined to facilitate evaluation of the backscatter frequency spectrum. An illustrative system response curve 36 is shown in FIG. 2. An illustrative backscatter signal 38 is shown obtained as a result of an acoustic pulse 34 covering a range of frequencies, such as up to about 2.5 MHz. The backscatter signal 38 exhibits large fluctuations with large peaks and valleys, which generally follow an expected exponential decay. The duration of the detectable backscatter signal depends upon the intensity of the pulse 34 and the magnitude of the encountered attenuation. For purposes of illustration, therefore, the duration of backscatter signal 38 may be of the order of about 30 microseconds. This is indicative of a depth of investigation of the order of about two to about three inches into the subsurface formation.

In the embodiment of FIG. 1 backscatter signals, such as 38, are applied on line 39 to a spectrum generator 40 which produces an output 42 a spectrum such as 44 in FIGS. 1A and 2 of the received backscatter signal 38. The spectrum 44 can be produced with a spectrum analyzer such as shown in U.S. Pat. No. 3,588,800; or with a Fast Fourier Transform operating on digital samples of the received backscatter signal 38. Digitizing of the latter may be obtained with a fast digital to analog converter. Generation of spectrum 44 can be done down hole in tool 10 or on the surface after transmission of the backscatter signal 38 along cable 16 to signal processor 20.

Any one backscatter signal 38 exhibits large signal fluctuations which are the result of voids or granular-caused interference. These fluctuations also occur in the frequency domain, or spectrum 44 of the backscatter signal 38 as shown in FIG. 1A. It is desirable to average the spectrum, not the amplitude domain, of the backscatter signal over a spatial region of the borehole 14 so that these fluctuations can be smoothed to produce useful signals. Preferably such averaging is done as the tool 10 is advanced along the borehole 14. The ultrasonic transducers 26 are pulsed quite rapidly, of the order of 100 times per second so that during such averaging, if done for a sufficient number of pulses, tool 10 will have moved a small distance. In effect, therefore, the averaging of spectra of the backscatter signals 38 is done over adjacent borehole regions.

For example, if tool 10 is moved at a rate of about 600 feet per hour and a transducer 26 is pulsed at a rate of 100 per second, the tool 10 will have moved about 0.2 inches if ten successive spectra are averaged.

The spectra on output 42 are thus applied to a running average generator 46. This device can be an appropriate accumulator capable of maintaining a running average of, for example, the preceeding ten amplitudes of each frequency component. With each new spectrum of a backscatter signal, the oldest is discarded and a new average generated. A plot of the frequency spectrum can be made concurrently on a recorder 48, for example, to form a variable density plot in which spectrum amplitude varies the intensity of the plot.

FIG. 2 has several other average amplitude frequency plots 50 and 52 illustrate various frequency dependencies of the subsurface formation. Plots 44 and 50 are of apparent similar shape, but of these plot 50 illustrates a sharper drop in amplitude as a function of frequency because the system response curve 36 indicates an increasing response as plot 50 drops off. With such strong drop-off in amplitude (representative of high attenuation), the formation region for which plot 50 was obtained is indicative of a fourth power behavior and a general indication of the granular property of the formation can be derived.

Plot 44 is indicative of a weaker attenuation illustrative of a change in granularity in the formation in comparison with that for the plot 50. Plot 52 shows a still weaker attenuation as a function of frequency indicative of a square power behavior. These attenuation variations can be attributed to changes in porosity or changes in the mean grain size. A correlation with a porosity log for the same zone may then resolve the variations in the plots as attributable to a change in the granularity of the subsurface formation. The plots 44, 50 and 52 can thus yield a determination of the frequency dependency of attenuation in the earth formation useful for deriving an indication of the grain size for a broad range of grain sizes and porosity conditions.

If angularly adjacent pads 26 yield, for the same frequency transducers 26, different frequency dependencies, such as for example, plots 44 and 52, then this may indicate different grain orientations. Conversely, similar plots are likely to be indicative of random grain orientations.

FIG. 4 shows a frequency plot 54, and an attenuation plot 55 which is normalized as to distance in the subsurface of different backscatter frequency dependencies. Over the frequency range from $f_1$ to $f_2$, the plot 54 exhibits an attenuation which appears to be weak and varies as a linear function of frequency, whereas at higher frequencies past $f_2$ the plot rapidly attenuates. The presence of the transition zone around $f_2$ may yield an indication of a granular condition for the formation to which the plot 54 relates or in comparison with similar plots of other zones a change in granularity. The techniques shown and described with reference to FIGS. 7, 8 and 9 enable a direct measurement of a transition in the frequency dependency of the subsurface attenuation by detecting a predetermined peak in the frequency domain of the backscatter signal. The frequency of such peak has been found to relate to the grain size in a determinable manner.

In FIG. 5 a technique 60, such as can be done with a digital signal processor, is illustrated. The backscatter signals on a line 39 are passed through times gates 62 to select different time intervals such as $T_1$ and $T_2$ in FIG. 1. Control signals for actuation of the time gates 62.1, 62.2 can be derived by a control 63 which detects the large acoustic reflection occurring at the wall 28 of the borehole 14. One may then select intervals $T_1$ and $T_2$ with suitable delays. The intervals $T_1$, $T_2$ may follow each other or occur during separate time periods and in some cases may partially overlap. The portion of the waveform during each interval is construed to be attributable from acoustic backscatter from a particular region inside the subsurface formation. The location is determined from the velocity of the acoustic backscatter. Such velocity can be obtained from previously obtained velocity logs for the same subsurface zones.

The selection of different time gates enables one to normalize the backscatter signal 38 as a function of distance in the subsurface formation and thus to obtain an indication of the frequency dependency of the attenuation inside the formation 12.

Hence, the outputs on lines 64 of gates 62 are coupled to spectrum generators 40 and thence to spatial averagers 46. A ratio former 66 then divides corresponding frequency components in the respective spectra. The output of the ratio former 66 is analyzed at 68 to determine the frequency dependency by comparing amplitudes of successive frequency components. This can be done by fitting a curve to the peaks of the frequency components or with a slope detector. A frequency transition is detected by sensing slope changes at 70.

In FIG. 6 an apparatus 80 is shown for generating spectra and producing a spectral average with techniques particularly useful for inside a tool 10. The backscatter signal on a line 39 is shown applied to interval selecting gates 62.1, 62.2 operated by control 63. A plurality of pass band filters 82 are coupled to the outputs 64 of gates 62. Filters 82 have different pass bands characterized by center frequencies at $f_1, f_2, \ldots f_n$ throughout the frequency bandwidth of interest.

The output of filters 82 are applied to integrators 84 which measure the energy in each signal from a filter. The signals on lines 86 from control 63 to gates 62 are combined in an OR gate 88 to reset the integrators just prior to allowing passage of a backscatter interval through a gate 62.

The outputs 90 of integrators 84 are each applied to a pair of sample and hold networks 92, 94 to respectively sample the amplitude of a frequency component in the intervals $T_1$ and $T_2$ of the backscatter signal. The actuation of the sample and hold networks 92, 94 is determined by the signals on lines 96 from control 63 and occur just at the end of each backscatter selection interval.

The sample and hold networks 92, 94 are each capable of accumulating signals from a number of samples so that, in effect, a spatial average can be accumulated. This average can be set, for example, for a fixed number of samples. After each sample, a small percentage reduction is then made to permit a running average as tool 10 is moved along the borehole 14. The reduction is a function of the extent of the average. If 10 samples are to be averaged, the reduction is one-tenth, if 15, then one-fifteenth, etc.

The reduction is achieved by control 63 which, after each sampling, produces a reduction control signal on line 98 to be applied to reduction inputs 100 on sample and hold networks 92, 94.

A suitable time after actuation of a control signal on line 98 as determined by a delay 102, divider networks 104 are actuated to form a ratio between the accumulated samples in pairs networks 92, 94. The ratio outputs on lines 106 represent the amplitude of the frequency components $f_1, f_2 \ldots f_n$.

An A/D converter 108 is provided to digitize the frequency component signals on lines 106 and enable further processing in digital signal processor for slope detection 110 and further analysis of the frequency dependency in analyzer 112.

With reference to FIGS. 7, 8 and 9, another acoustic backscatter technique is shown for measuring a granularity property of the subsurface formation by detecting a peak in a predetermined frequency domain of the backscatter signal. When a wide frequency acoustic pulse is employed at backscatter frequencies including wavelengths which are approximately the same as the subsurface formation grain diameters, the backscatter spectrum was found characterized by a dominant peak. The frequency of this peak occurs generally at that portion of the spectrum where the attentuation attributable to scattering exhibits a change in dependency as a function of frequency from $\overline{d}^3 f^4$ to $\overline{d} f^2$, and also is nearby a characteristic frequency related to the mean grain diameter $\overline{d}$ as set forth below.

The basic acoustic relationship $f\lambda = v$ also holds at backscatter frequencies, with f representing frequency, $\lambda$ the wavelength, and v the velocity of the compressional wave through the subsurface formation. At frequencies where the attenuation frequency dependency changes from $f^4$ to $f^2$, the wavelength $\lambda$ can be approximately related to the mean characteristic grain dimension $\overline{d}$, by $k = 2A/\overline{d}$ where $k = 2\pi/\lambda$ and A is a constant having a value in the range from about 1 to 2 depending upon various scattering processes. In this backscatter frequency range, therefore, a characteristic frequency, $f_c$, exists where the mean grain diameter, $\overline{d}$, can be related to the characteristic frequency generally according to the relationship $\overline{d} = vA/\pi f_c$. This relationship is approximate and depends upon a number of factors involved in acoustic backscatter as well as when the subsurface formation includes many different grain sizes.

FIG. 7 shows a curve 120 representative of an average frequency plot of acoustic backscatter for adjacent borehole regions such as may be obtained at output 47 of averager network 46 in FIG. 9.

Normally, i.e. without averaging, the frequency spectrum of the backscatter signal is characterized by sharp and large fluctuations as shown in FIG. 1A, whereby fundamental trends such as peaks 122, 124 in FIG. 7 are obscured. For purposes of illustration, the curve 120 is shown smoother from what would normally be achieved with practical averaging of backscatter signals from adjacent borehole regions.

The frequency response of the system employed to obtain an acoustic backscatter signal tends to strongly affect the shape of a spectrum such as 120, particularly when the acoustic investigation is carried out over a broad frequency range. For example, curve 126 represents the frequency response or transfer function of the transducer and amplifiers, both for transmittal and reception, with which curve 120 was obtained. When the curves 120, 126 are placed on the same plot, it is apparent that the second peak 124 appears to be more attributable to equipment effects that related to subsurface formation characteristics. This can be confirmed when the backscatter spectrum response 120 is modified to adjust for the influence by the equipment frequency response as represented by curve 126.

The modified backscatter spectrum may have an appearance such as represented by curve 128 in FIG. 8. Curve 128 exhibits a dominant peak 130 at a frequency of about 1.0 MHz. Such peak 130 may be detectable even in the presence of large signal fluctuations by using signal processing techniques and the frequency of the detected peak can be used to provide an indication of the granularity property of the subsurface formation. The spread of the spectral peak such as 130, i.e. its bandwidth, may also provide an indication of the distribution of particle sizes.

FIG. 9 shows an illustrative system 132 for deriving an indication of granular sizes or distribution. The detected backscatter signal is shown applied to a spectrum generator 40 and a spatial averager 46. As previously mentioned, these functions may be provided with a digital signal processor. A storage network 134 is provided, in which the overall frequency response of the transducers and amplifiers for the acoustic backscatter investigation is stored. The frequency response, for example, may constitute a number of amplitude values at discrete small frequency intervals and when plotted would provide an envelope as illustrated by curve 126 in FIG. 7. Since a broad range of frequencies may be investigated, a plurality of transducers and corresponding frequency responses may be stored in network 134.

The amplitude of the frequency responses may be substantially out of scale with the amplitudes of the backscatter spectra, even after the latter's amplification. Accordingly, a peak value of averaged spectra is measured with a peak detector 136 and applied to an amplitude adjusting network 138. The latter provides an overall gain adjustment to the appropriate frequency response values used from network 134 so as to provide generally comparable frequency domain signals, such as presented by curves 120, 126 in FIG. 7.

The outputs, 140 from amplitude adjusting network 138 and averaged spectra on line 47, are combined in a spectrum modifier network 142 to correct the averaged backscatter spectra for effects by the frequency response of the equipment used to conduct the acoustic backscatter investigation. The modifier network 142 may have various forms. One technique for modifier network 140 is shown in FIG. 9 and measures the difference with a difference network 146 between the amplitudes of the response frequencies and a constant value, such as a peak value, $P_k$, at 144 in FIG. 7. The differences are then added to the amplitude values of corresponding frequencies in the backscatter spectrum in a summing network 148.

The output 150 of modifier network 142 may be a spectrum such as 130 or 152 in FIG. 8. However, more likely a spectrum having sharp peaks and valleys as shown at 154 would be obtained. Such modified spectrum 154 still exhibits a characteristic or dominant peak such as at 156 and this can be detected with signal processing techniques.

The output 150 of spectrum modifier 150 is shown coupled to a peak detector 160 for identifying peaks 130, 156 and 162 in spectra such as shown in FIG. 8. The peak detector 160 for this purpose preferably is a signal processor. The output of the peak detector 160 is used in a network 164 to determine the frequency of the detected peak. The peak's frequency value, $f_p$, may then be recorded and used to derive a value of the mean grain diameter, $\bar{d}$, in a detector network 166. The latter determines the value for $\bar{d}$ according to the relationship $\bar{d} = vA/\pi f_p$ where the value for v is obtained from a previous compressional acoustic velocity log for the same borehole depth. The value of $\bar{d}$ appears on an output 168 and may be recorded.

An indication of the distribution of grain sizes can be derived by, for example, measuring the bandwidth of the modified spectra on line 150. The bandwidth is measured with a detector 170, which scans the values of the modified spectra on both sides of the measured peak's frequency $f_p$ to determine where the spectra drops below a predetermined level, such as 3 db, below the peak.

The detection of peaks 130, 162 and 156 may not precisely yield the correct mean grain diameter $\bar{d}$ from network 166. For example, the spectra 128, 152 and 154 were obtained from experiments in which the mean grain diameters were respectively 0.8, 0.56 and 0.26 mm. The characteristic frequencies, $f_c$, related to such grain dimensions should be at frequencies identified at 172, 174 and 176 in FIG. 8 and thus are spaced from the spectral peaks. However, the separation of these characteristic frequencies from the peaks in the spectra is not large so that the backscatter spectrum peaks can be used as an indication of grain sizes, and if bandwidths are measured, an indication of grain size distribution.

Having thus described several embodiments for deriving a subsurface formation parameter which characterizes a granularity property of the formation, the advantages of the invention can be appreciated. Variations from the described embodiments can be made without departing from the scope of the invention.

What is claimed is:

1. In a method for determining a subsurface formation parameter which characterizes a granularity property of a subsurface formation around a borehole comprising the steps of directing like pulses of ultrasonic energy from inside the borehole at the subsurface formation with frequency bandwidths selected to produce acoustic backscatter from grains in the formation, the range of acoustic frequencies in said pulses being selected such that the acoustic backscatter from inside the formation includes frequencies which attenuate in a manner which is charactertistic of a granularity property of the subsurface formation for a broad range of formation grain sizes and formation porosity conditions; and detecting said acoustic backscatter produced by said pulses of ultrasonic energy.

2. The method for determining a subsurface formation parameter characteristic of a granularity property of the subsurface formation as set forth in claim 1 and further including the steps of forming frequency spectra of the detected backscatter produced by said pulses; and deriving from said spectra an indication of the frequency dependency of attenuation in the acoustic backscatter and the frequency range in which said dependency occurs.

3. The method for determining a subsurface formation parameter characteristic of a granularity property of the subsurface formation as set forth in claim 2 wherein said frequency spectra forming step includes the step of averaging spectra attributable to backscatter from adjacent regions of the formation.

4. The method for determining a subsurface formation parameter characteristic of a granularity property of the subsurface formation as set forth in claim 1 and further including the step of forming frequency spectra of the detected acoustic backscatter generated by said pulses; and deriving from said spectra a frequency representative of a transition between frequency ranges whose amplitudes exhibit different frequency dependencies.

5. The method for determining a subsurface formation parameter characteristic of a granularity property of the subsurface formation as set forth in claim 1 and further including the steps of selecting a first portion of the detected acoustic backscatter occurring during a first interval thereof;

generating a frequency spectrum of said first portion to identify the amplitude of frequency components in the first portion;

selecting a second portion of the detected acoustic backscatter occurring during a second interval thereof;

generating a frequency spectrum of said second portion to identify the amplitude of frequency components therein;

spatially averaging said spectra of the first and second portions over adjacent subsurface formation regions;

forming ratios between corresponding frequency components of said spectra; and deriving from said ratios an indication of the frequency dependency of the scatter attenuation for said adjacent subsurface formation regions.

6. The method for determining a subsurface formation parameter characteristic of a granularity property of the subsurface formation as set forth in claim 5 wherein said frequency dependency deriving step further includes the steps of comparing amplitudes of frequency components; and determining from said comparing step a frequency representative of a transition range between spectral ranges whose amplitudes exhibit different frequency dependencies.

7. In a method for determining a subsurface formation parameter which characterizes a granularity property of the subsurface formation around a borehole comprising the steps of forming frequency spectra of signals representative of acoustic backscatter produced by like pulses of ultrasonic energy directed from inside the borehole at the subsurface formation with frequency bandwidths selected to cause said acoustic backscatter from grains in the formation, the range of acoustic frequencies in said pulses being selected such that the acoustic backscatter from inside the formation includes frequencies which attenuate in a manner which is characteristic of a granularity property of the subsurface formation for a broad range of formation grain sizes and formation porosity conditions; and deriving from said spectra a measure of the frequency dependency of the attenuation and the frequency range in which said measured dependency occurs.

8. The method for determining a subsurface formation parameter characteristic of a granularity property of the subsurface formation as set forth in claim 7 and further including the step of deriving from said spectra a frequency representative of a transition between spectral ranges whose amplitudes exhibit different frequency dependencies.

9. The method for determining a subsurface formation parameter characteristic of a granularity property of the formation as set forth in claim 7 wherein said sprectra forming step includes the step of averaging spectra produced from acoustic backscatter from adjacent regions of the subsurface formation.

10. The method of determining a subsurface formation parameter characteristic of a granularity property of the formation as set forth in claim 9 wherein said averaging step averages spectra produced from acoustic backscatter originating from vertically adjacent regions of the formation.

11. The method of determining a subsurface formation parameter characteristic of a granularity property of the formation as set forth in claim 7 wherein the frequency spectra deriving step further includes the steps of selecting a first portion of one backscatter signal during a first interval thereof;

generating a frequency spectrum of said first portion to determine the amplitude of frequency components therein;

selecting a second portion of said one backscatter signal during a second interval thereof;

generating a frequency spectrum of said second portion to determine the amplitude of frequency components therein;

spatially averaging said spectra of the first and second portions over adjacent subsurface formation regions;

forming ratios between corresponding frequency components of said spectra; and deriving from said ratios an indication of the frequency dependency of the scatter attenuation for said adjacent subsurface formation regions.

12. An apparatus for deriving a subsurface formation parameter which characterizes a granularity property of the subsurface formation around a borehole comprising means for producing like pulses of ultrasonic energy from inside the borehole at the subsurface formation with frequency bandwidths selected to produce acoustic backscatter from grains in the subsurface formation, the range of acoustic frequencies in said pulses being selected such that the acoustic backscatter from inside the formation includes frequencies which attenuate in a manner which is characteristic of a granularity property of the subsurface formation and detecting the acoustic backscatter produced by said pulses;

means responsive to signals representative of said detected acoustic backscatter for generating frequency spectra thereof with frequency component signals whose amplitudes represent said frequency dependency; and means for deriving said frequency dependency from said frequency spectra.

13. The apparatus for deriving a subsurface formation parameter as set forth in claim 12 wherein said spectra generating means includes means for averaging said spectra over adjacent regions of the subsurface formation.

14. The apparatus for deriving a subsurface formation parameter as set forth in claim 13 wherein said spectra generating means further includes means for generating a first spectrum formed of frequency component signals for a first interval of one acoustic backscatter signal;

means for generating a second spectrum formed of frequency component signals for a second interval of said one acoustic backscatter signal; and means for forming ratios between corresponding frequency component signals in said first and second spectra to produce a backscatter spectrum which is normalized as to a predetermined distance in the subsurface formation.

15. The apparatus for deriving a formation parameter as set forth in claim 13 wherein frequency spectra generating means includes a plurality of passband filters having passbands distributed across the bandwidth of said pulses of ultrasonic energy.

16. An acoustic investigation method for obtaining a measurement of a granularity property of a subsurface formation with an ultrasonic investigation tool located in a borehole penetrating the formation, comprising the steps of directing pulses of ultrasonic energy from inside the borehole at the subsurface formation with a frequency bandwidth selected to produce acoustic backscatter from grains inside the formation with wavelengths of the order of the mean diameter of grains in the subsurface formation;

detecting said acoustic backscatter produced by said pulses of ultrasonic energy;

forming a frequency spectrum of the detected acoustic backscatter produced by said pulses;

deriving from said backscatter frequency spectrum an indication of said granularity property of the subsurface formation.

17. The method for obtaining a measurement of a granularity property of a subsurface formation as set forth in claim 16 wherein said deriving step further includes detecting a peak in the frequency spectrum in the frequency vicinity where the frequency dependency of the subsurface formation attenuation changes as a function of $\overline{d}^3 f^4$ to a function of $\overline{d} f^2$; and determining the frequency of said peak as an indication of said granularity property.

18. The method for obtaining a measurement of a granularity property of a subsurface formation as set forth in claim 16 wherein said deriving step further includes determining as an indication of said granularity property the bandwidth of the frequency spectrum in the frequency vicinity where the frequency dependency of the subsurface formation attenuation changes as a function of $\overline{d}^3 f^4$ to a function of $\overline{d} f^2$.

19. An acoustic investigation method for obtaining a measurement of a granularity property of a subsurface formation with an ultrasonic investigation tool located in a borehole penetrating the formation, comprising the steps of directing pulses of ultrasonic energy from inside the borehole at the subsurface formation with a frequency bandwidth selected to produce acoustic backscatter from grains inside the formation with wavelengths of the order of the mean diameter of grains in the subsurface formation;

detecting said acoustic backscatter produced by said pulses of ultrasonic energy;

forming a frequency spectrum of the detected acoustic backscatter produced by said pulses;

modifying said frequency spectrum to remove the effect of the frequency response of the tool within the selected frequency bandwidth; and deriving an indication of said granularity property from said modified frequency spectrum.

20. The method of obtaining a measurement of a granularity property of a subsurface formation as set forth in claim 19 wherein said deriving step further comprises measuring the frequency of a peak in the modified frequency spectrum.

21. The method for obtaining a measurement of a granularity property of a subsurface formation as set forth in claim 20 wherein said deriving step still further comprises generating a signal representative of the acoustic velocity of the subsurface earth formation to which the modified frequency spectrum relates; and determining an indication of the mean grain size of the subsurface earth formation as a function of said peak frequency and said acoustic velocity in accordance with a predetermined relationship.

22. The method for obtaining a measurement of a granularity property of a subsurface formation as set forth in claim 19 wherein said deriving step further comprises measuring the bandwidth of a peak in the frequency spectrum as an indication of the distribution of grain sizes in said subsurface earth formation.

23. The method for obtaining a measurement of a granularity property of a subsurface formation as set forth in claim 19 wherein said modifying step further comprises generating a response signal proportional to the frequency response of said tool in said selected frequency bandwidth; and applying the adjusted response signal to modify said frequency spectrum to remove the effect of the frequency response of the tool therefrom.

24. An acoustic investigation method for obtaining a measurement of a granularity property of a subsurface formation with an ultrasonic investigation tool located in a borehole penetrating the formation comprising the steps of
- directing pulses of ultrasonic energy from a transducer inside the borehole at the subsurface earth formation with a frequency bandwidth selected to produce acoustic backscatter from grains inside the formation and detecting said acoustic backscatter produced by said pulses of ultrasonic energy with said transducer;
- forming frequency spectra of the detected acoustic backscatter produced by said pulses;
- averaging spectra attributable to backscatter from adjacent regions of the subsurface formation to form an averaged spectrum;
- modifying said frequency spectrum to remove the effect of the frequency response of the transducer within said selected frequency bandwidth;
- detecting a peak in said modified frequency spectrum;
- determining the frequency of said peak; and
- deriving from the determined peak frequency an indication of the grain sizes of said subsurface formation.

25. The method for obtaining a measurement of a granularity property of a subsurface formation as set forth in claim 24 wherein said deriving step further comprises
- measuring the frequency bandwidth of said peak as an indication of granular distribution in said subsurface formation.

26. An apparatus for obtaining an indication of a granularity property of a subsurface formation with an ultrasonic investigation tool comprising
- means for producing pulses of ultrasonic energy from inside the borehole at the subsurface formation with a frequency bandwidth selected to produce acoustic backscatter from grains inside the formation with wavelengths of the order of the mean diameter of grains in the subsurface formation and detecting said acoustic backscatter produced by said pulses of ultrasonic energy;
- means for producing a frequency spectrum of the detected backscatter produced by said pulses of ultrasonic energy; and
- means responsive to said frequency spectrum for generating a signal representative of said granularity property of the subsurface formation.

27. The apparatus for obtaining said granularity property as set forth in claim 26 wherein said signal generating means further includes
- means for detecting a peak in the frequency spectrum where the frequency dependency of the subsurface formation attenuation changes as a function of $\bar{d}^3 f^4$ to a function of $\bar{d} f^2$; and
- means for obtaining the frequency of said peak as an indication of said granularity property.

28. The apparatus for measuring said granularity property as set forth in claim 26 wherein said signal generating means further includes
- means for producing a signal indicative of the bandwidth of said frequency spectrum.

* * * * *